US011327773B2

United States Patent
Hermosillo Valadez et al.

(10) Patent No.: US 11,327,773 B2
(45) Date of Patent: May 10, 2022

(54) ANATOMY-AWARE ADAPTATION OF GRAPHICAL USER INTERFACE

(71) Applicant: Siemens Healthcare GmbH, Erlangen (DE)

(72) Inventors: Gerardo Hermosillo Valadez, West Chester, PA (US); Zhigang Peng, Ambler, PA (US)

(73) Assignee: Siemens Healthcare GmbH, Erlangen (DE)

( * ) Notice: Subject to any disclaimer, the term of this patent is extended or adjusted under 35 U.S.C. 154(b) by 232 days.

(21) Appl. No.: 15/977,188

(22) Filed: May 11, 2018

(65) Prior Publication Data
US 2019/0171467 A1 Jun. 6, 2019

Related U.S. Application Data

(60) Provisional application No. 62/594,638, filed on Dec. 5, 2017.

(51) Int. Cl.
| | |
|---|---|
| *G06F 9/451* | (2018.01) |
| *G16H 30/20* | (2018.01) |
| *G06F 3/0482* | (2013.01) |
| *G06K 9/62* | (2022.01) |
| *G06N 3/08* | (2006.01) |
| *G06N 20/00* | (2019.01) |
| *G06V 40/10* | (2022.01) |
| *G06F 9/445* | (2018.01) |

(52) U.S. Cl.
CPC ............ *G06F 9/451* (2018.02); *G06F 3/0482* (2013.01); *G06K 9/6201* (2013.01); *G06N 3/08* (2013.01); *G06N 20/00* (2019.01); *G06V 40/10* (2022.01); *G16H 30/20* (2018.01); *G06F 9/44505* (2013.01)

(58) Field of Classification Search
CPC .... G06F 9/451; G06F 3/0482; G06F 9/44505; G06N 20/00; G06N 3/08; G06N 3/0454; G06K 9/6201; G06K 9/00362; G06K 2209/05; G16H 30/20; G16H 30/40; G16H 50/20; G16H 40/63; G06T 2207/10116; G06T 2207/20084; G06T 2200/24; G06T 2207/10072; G06T 7/0012; G06V 40/10
See application file for complete search history.

(56) References Cited

U.S. PATENT DOCUMENTS

| | | | | |
|---|---|---|---|---|
| 11,151,721 | B2* | 10/2021 | Avendi | G06K 9/726 |
| 2008/0260226 | A1* | 10/2008 | Moriya | G06K 9/6201 |
| | | | | 382/128 |
| 2009/0034813 | A1* | 2/2009 | Dikmen | G06T 7/74 |
| | | | | 382/131 |
| 2009/0044134 | A1* | 2/2009 | Cave | G06F 40/166 |
| | | | | 715/762 |
| 2015/0261915 | A1* | 9/2015 | Yanagida | G06F 16/5866 |
| | | | | 382/131 |

(Continued)

*Primary Examiner* — Kieu D Vu
*Assistant Examiner* — Blaine T. Basom

(57) ABSTRACT

A framework for anatomy-aware adaptation of a graphical user interface. Landmarks are first detected by passing one or more current images through a trained machine learning model. A body section may then be inferred based on the detected landmarks. One or more user interface elements may be determined based on the inferred body section. A graphical user interface may then be adapted with the determined one or more user interface elements.

18 Claims, 5 Drawing Sheets

(56) References Cited

U.S. PATENT DOCUMENTS

| | | | |
|---|---|---|---|
| 2016/0098832 A1* | 4/2016 | Yoo | G06T 7/0012 |
| | | | 382/131 |
| 2016/0306924 A1* | 10/2016 | Singh | G16H 30/20 |
| 2017/0372473 A1* | 12/2017 | Ujiie | G06F 3/0482 |
| 2018/0032801 A1* | 2/2018 | Gur | G06K 9/4628 |
| 2019/0057501 A1* | 2/2019 | Lo | G06T 7/11 |
| 2019/0125298 A1* | 5/2019 | Abolmaesumi | G06N 3/08 |

* cited by examiner

ANATOMY-AWARE ADAPTATION OF GRAPHICAL USER INTERFACE

CROSS REFERENCE TO RELATED APPLICATIONS

This application claims priority to U.S. Provisional Application No. 62/594,638 filed Dec. 5, 2017, the entire contents of which are hereby incorporated by reference.

TECHNICAL FIELD

The present disclosure generally relates to digital image data processing, and more particularly to anatomy-aware adaptation of a graphical user interface.

BACKGROUND

The field of medical imaging has seen significant advances since the time X-Rays were first used to determine anatomical abnormalities. Medical imaging hardware has progressed from modern machines, such as Magnetic Resonance (MR) imaging scanners, Computed Tomographic (CT) scanners and Positron Emission Tomographic (PET) scanners, to multimodality imaging systems such as PET-CT and PET-MRI systems. Because of large amount of image data generated by such modern medical scanners, there has been and remains a need for developing image processing techniques that can automate some or all of the processes to determine the presence of anatomical abnormalities in scanned medical images.

Digital medical images are constructed using raw image data obtained from a scanner, for example, a computerized axial tomography (CAT) scanner, magnetic resonance imaging (MRI), etc. Digital medical images are typically either a two-dimensional ("2D") image made of pixel elements, a three-dimensional ("3D") image made of volume elements ("voxels") or a four-dimensional ("4D") image made of dynamic elements ("doxels"). Such 2D, 3D or 4D images are processed using medical image recognition techniques to determine the presence of anatomical abnormalities or pathologies, such as cysts, tumors, polyps, etc. Given the amount of image data generated by any given image scan, it is preferable that an automatic technique should point out anatomical features in the selected regions of an image to a doctor for further diagnosis of any disease or condition.

Automatic image processing and recognition of structures within a medical image are generally referred to as Computer-Aided Detection (CAD). A CAD system can process medical images, localize and segment anatomical structures, including possible abnormalities (or candidates), for further review. Recognizing anatomical structures within digitized medical images presents multiple challenges. For example, a first concern relates to the accuracy of recognition of anatomical structures within an image. A second area of concern is the speed of recognition. Because medical images are an aid for a doctor to diagnose a disease or condition, the speed with which an image can be processed and structures within that image recognized can be of the utmost importance to the doctor in order to reach an early diagnosis.

Graphical user interfaces are often used to display digitized medical images for image interpretation and manipulation. Traditional graphical user interfaces are often designed with a "one-size-fits-all" approach, with a standard set of tools and other user interface elements for all types of image modalities and anatomies. These tools and other user interface elements may not necessarily by relevant to the image being displayed, resulting in too much clutter on the screen that slows down the workflow of the user.

SUMMARY

Described herein is a framework for anatomy-aware adaptation of a graphical user interface. Landmarks are first detected by passing one or more current images through a trained machine learning model. A body section may then be inferred based on the detected landmarks. One or more user interface elements may be determined based on the inferred body section. A graphical user interface may then be adapted with the determined one or more user interface elements.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings.

DETAILED DESCRIPTION

Figure 1:
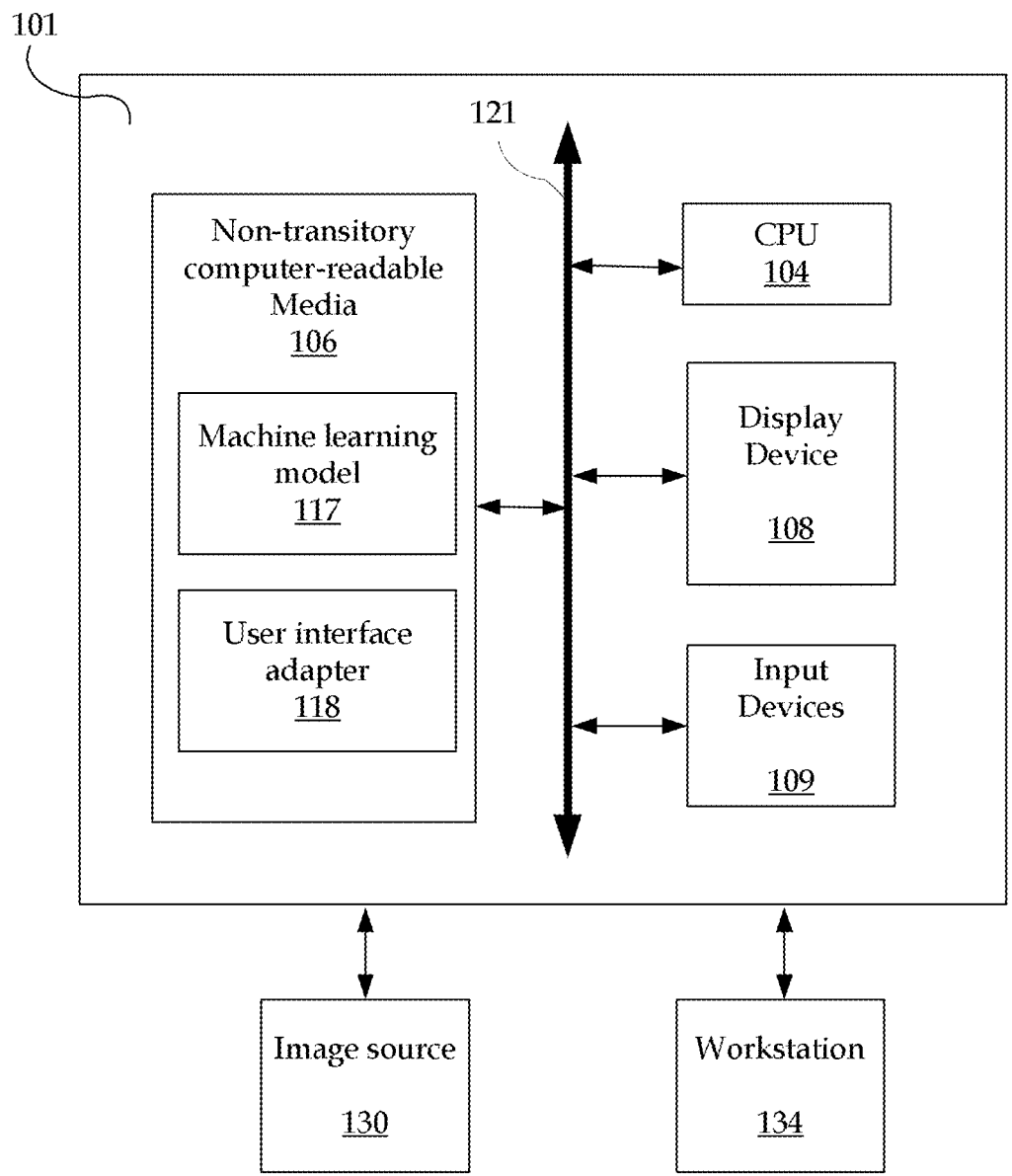
FIG. 1 is a block diagram illustrating an exemplary system.

In the following description, numerous specific details are set forth such as examples of specific components, devices, methods, etc., in order to provide a thorough understanding of implementations of the present framework. It will be apparent, however, to one skilled in the art that these specific details need not be employed to practice implementations of the present framework. In other instances, well-known materials or methods have not been described in detail in order to avoid unnecessarily obscuring implementations of the present framework. While the present framework is susceptible to various modifications and alternative forms, specific embodiments thereof are shown by way of example in the drawings and will herein be described in detail. It should be understood, however, that there is no intent to limit the invention to the particular forms disclosed; on the contrary, the intention is to cover all modifications, equivalents, and alternatives falling within the spirit and scope of the invention. Furthermore, for ease of understanding, certain method steps are delineated as separate steps; however, these separately delineated steps should not be construed as necessarily order dependent in their performance.

The term "x-ray image" as used herein may mean a visible x-ray image (e.g., displayed on a video screen) or a digital representation of an x-ray image (e.g., a file corresponding to the pixel output of an x-ray detector). The term "in-treatment x-ray image" as used herein may refer to images captured at any point in time during a treatment delivery phase of an interventional or therapeutic procedure, which may include times when the radiation source is either on or off. From time to time, for convenience of description, CT imaging data (e.g., cone-beam CT imaging data) may be used herein as an exemplary imaging modality. It will be appreciated, however, that data from any type of imaging modality including but not limited to high-resolution computed tomography (HRCT), x-ray radiographs, MRI, PET (positron emission tomography), PET-CT, SPECT, SPECT-CT, MR-PET, 3D ultrasound images or the like may also be used in various implementations.

Unless stated otherwise as apparent from the following discussion, it will be appreciated that terms such as "segmenting," "generating," "registering," "determining," "aligning," "positioning," "processing," "computing," "selecting," "estimating," "detecting," "tracking" or the like may refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices. Embodiments of the methods described herein may be implemented using computer software. If written in a programming language conforming to a recognized standard, sequences of instructions designed to implement the methods can be compiled for execution on a variety of hardware platforms and for interface to a variety of operating systems. In addition, implementations of the present framework are not described with reference to any particular programming language. It will be appreciated that a variety of programming languages may be used.

As used herein, the term "image" refers to multi-dimensional data composed of discrete image elements (e.g., pixels for 2D images and voxels for 3D images). The image may be, for example, a medical image of a subject collected by computer tomography, magnetic resonance imaging, ultrasound, or any other medical imaging system known to one of skill in the art. The image may also be provided from non-medical contexts, such as, for example, remote sensing systems, electron microscopy, etc. Although an image can be thought of as a function from $R^3$ to R, or a mapping to $R^3$, the present methods are not limited to such images, and can be applied to images of any dimension, e.g., a 2D picture or a 3D volume. For a 2- or 3-dimensional image, the domain of the image is typically a 2- or 3-dimensional rectangular array, wherein each pixel or voxel can be addressed with reference to a set of 2 or 3 mutually orthogonal axes. The terms "digital" and "digitized" as used herein will refer to images or volumes, as appropriate, in a digital or digitized format acquired via a digital acquisition system or via conversion from an analog image.

The terms "pixels" for picture elements, conventionally used with respect to 2D imaging and image display, and "voxels" for volume image elements, often used with respect to 3D imaging, can be used interchangeably. It should be noted that the 3D volume image is itself synthesized from image data obtained as pixels on a 2D sensor array and displayed as a 2D image from some angle of view. Thus, 2D image processing and image analysis techniques can be applied to the 3D volume image data. In the description that follows, techniques described as operating upon pixels may alternately be described as operating upon the 3D voxel data that is stored and represented in the form of 2D pixel data for display. In the same way, techniques that operate upon voxel data can also be described as operating upon pixels. In the following description, the variable x is used to indicate a subject image element at a particular spatial location or, alternately considered, a subject pixel. The terms "subject pixel" or "subject voxel" are used to indicate a particular image element as it is operated upon using techniques described herein.

A framework for automatically adapting a graphical user interface based on the anatomy represented in an image is presented herein. Depending on the different organs or body sections present in different medical image modalities (e.g., CT or MR), different user interface elements may be dynamically selected and presented to the user. More particularly, the framework may analyze the image loaded via the user interface and employ machine learning methods to identify the anatomical section of the body that is present in the image. Relevant user interface elements (e.g., tools, functions) that are targeted to this part of the anatomical section may then be identified and displayed in the graphical user interface. These and other features and advantages will be described in more details herein.

FIG. 1 is a block diagram illustrating an exemplary system 100. The system 100 includes a computer system 101 for implementing the framework as described herein. In some implementations, computer system 101 operates as a standalone device. In other implementations, computer system 101 may be connected (e.g., using a network) to other machines, such as image source 130 and workstation 134. In a networked deployment, computer system 101 may operate in the capacity of a server (e.g., thin-client server), a cloud computing platform, a client user machine in server-client user network environment, or as a peer machine in a peer-to-peer (or distributed) network environment.

In some implementations, computer system 101 comprises a processor or central processing unit (CPU) 104 coupled to one or more non-transitory computer-readable media 106 (e.g., computer storage or memory), display device 108 (e.g., monitor) and various input devices 109 (e.g., mouse or keyboard) via an input-output interface 121. Computer system 101 may further include support circuits such as a cache, a power supply, clock circuits and a communications bus. Various other peripheral devices, such as additional data storage devices and printing devices, may also be connected to the computer system 101.

The present technology may be implemented in various forms of hardware, software, firmware, special purpose processors, or a combination thereof, either as part of the microinstruction code or as part of an application program or software product, or a combination thereof, which is executed via the operating system. In some implementations, the techniques described herein are implemented as computer-readable program code tangibly embodied in non-transitory computer-readable media 106. In particular, the present techniques may be implemented by machine learning model 117 and user interface adapter 118.

Non-transitory computer-readable media 106 may include random access memory (RAM), read-only memory (ROM), magnetic floppy disk, flash memory, and other types of memories, or a combination thereof. The computer-readable program code is executed by CPU 104 to process medical data retrieved from, for example, image source 130. As such, the computer system 101 is a general-purpose computer system that becomes a specific purpose computer system when executing the computer-readable program code. The computer-readable program code is not intended to be limited to any particular programming language and implementation thereof. It will be appreciated that a variety of programming languages and coding thereof may be used to implement the teachings of the disclosure contained herein.

The same or different computer-readable media 106 may be used for storing a database (or dataset). Such data may also be stored in external image source 130 or other memories. Image source 130 may store medical images acquired by a radiology imaging device (e.g., MR or CT scanner).

Image source 130 may be implemented using a database management system (DBMS) managed by the CPU 104 and residing on a memory, such as a hard disk, RAM, or removable media. Image source 130 may be implemented on one or more additional computer systems. For example, image source 130 may include a data warehouse system residing on a separate computer system, a cloud platform or system, a picture archiving and communication system (PACS), or any other hospital, medical institution, medical office, testing facility, pharmacy or other medical patient record storage system.

The workstation 134 may include a computer and appropriate peripherals, such as a keyboard and display device, and can be operated in conjunction with the entire system 100. For example, the workstation 134 may communicate directly or indirectly with the image source 130 so that the medical image data can be rendered at the workstation 134 and viewed on a display device. The workstation 134 may also provide other types of medical data of a given patient. The workstation 134 may include a graphical user interface to receive user input via an input device (e.g., keyboard, mouse, touch screen voice or video recognition interface, etc.).

It is to be further understood that, because some of the constituent system components and method steps depicted in the accompanying figures can be implemented in software, the actual connections between the systems components (or the process steps) may differ depending upon the manner in which the present framework is programmed. Given the teachings provided herein, one of ordinary skill in the related art will be able to contemplate these and similar implementations or configurations of the present framework.

Figure 2A:
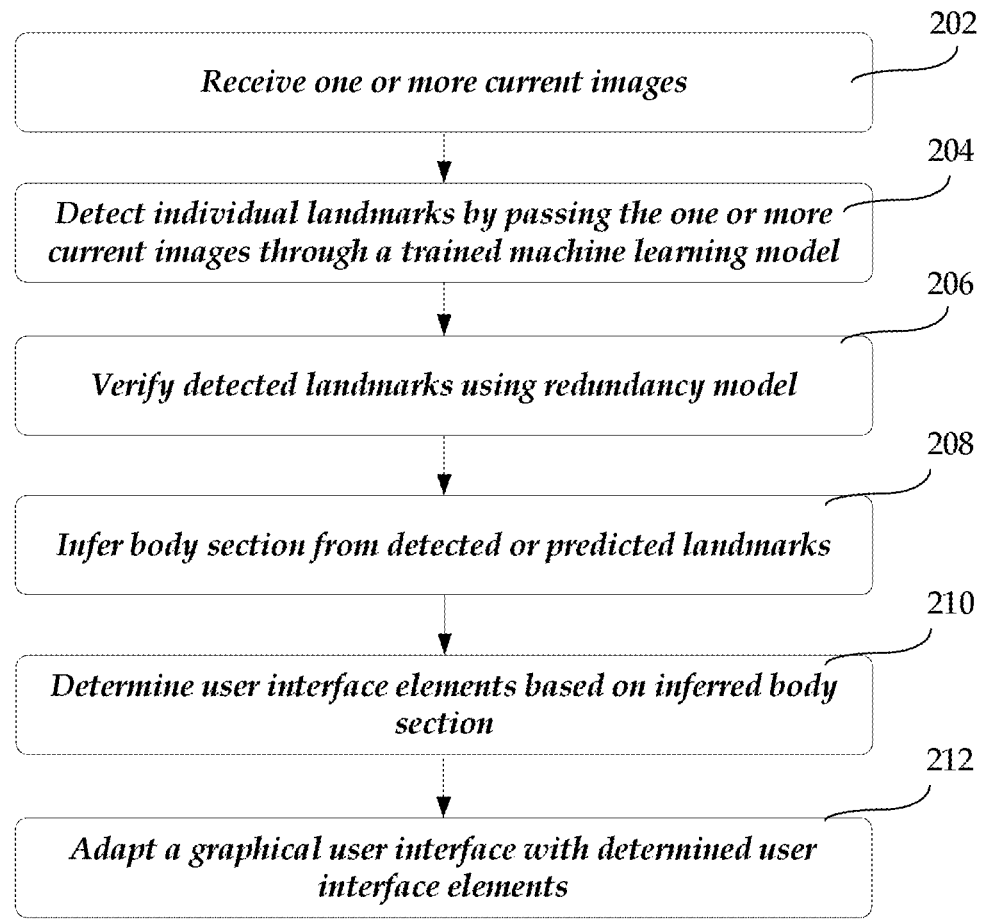
FIG. 2A shows an exemplary method of graphical user interface adaptation by a computer system.

FIG. 2A shows an exemplary method 200 of graphical user interface adaptation by a computer system. It should be understood that the steps of the method 200 may be performed in the order shown or a different order. Additional, different, or fewer steps may also be provided. Further, the method 200 may be implemented with the system 100 of FIG. 1, a different system, or a combination thereof.

At 202, user interface adapter 118 receives one or more current images. The one or more current images may be, for example, selected by a user via a user interface of a medical image interpretation software implemented at workstation 134. The one or more current images may be retrieved from image source 130 (or any other sources), loaded and displayed via the user interface at workstation 134. The one or more current images may be, for example, two-dimensional images extracted from three-dimensional (3D) image data of a region of interest. The one or more current images may represent a sagittal, coronal or axial view of the region of interest. The one or more current images may also include any other number of dimensions, such as 3D or 4D. The one or more current images are acquired by an imaging modality, such as magnetic resonance (MR) imaging, computed tomography (CT), high-resolution computed tomography (HRCT), helical CT, X-ray, angiography, positron emission tomography (PET), fluoroscopy, ultrasound, single photon emission computed tomography (SPECT), or a combination thereof.

At 204, user interface adapter 118 detects one or more individual landmarks in the one or more current images. A landmark may be any individual point with anatomical significance or biological meaning in an organism. The landmark is typically an easily identifiable feature point. The landmark may be manually or "fuzzily" annotated by machine. Examples of landmarks include, but are not limited to, head and neck landmarks (e.g., orbital bone, superior temporal line, inferior temporal line, frontal process, coronal suture), spine landmarks (e.g., T1, T7, T12) and cardiac landmarks (e.g., aortic valve, tricuspid valve, pulmonary valve, mitral valve).

The individual landmarks may be detected by passing the current image through a trained machine learning model 117. The machine learning model 117 may be trained to recognize individual anatomical landmarks in an image acquired by a specific image modality. The machine learning model 117 may be, for example, a deep learning architecture that includes stacked layers of learning nodes. The machine learning model 117 may include, for example, a convolutional neural network (CNN) classifier or any other type of classifier. The machine learning model 117 may be trained with, for example, training images with annotated landmarks. Different sets of training images acquired by different imaging modalities may be used to train the machine learning model 117.

At 206, user interface adapter 118 verifies the detected landmarks by using a redundancy model to predict landmarks. More particularly, user interface adapter 118 may verify the landmarks detected in the previous step 204 by using the redundancy model to predict landmarks and comparing the predicted landmarks with the detected landmarks to determine if the detection is reliable. If the location of a landmark predicted by the redundancy model does not match the location of the detected landmark, the detection is deemed unreliable and the predicted location is considered as valid and used in the next step 208. Otherwise, if a match is found, the detected landmark is deemed valid and used in the next step 208.

In the redundancy model, several individual landmarks are combined to add redundancy to the framework. More particularly, several subsets of the whole set of landmarks representing the entire body are defined. Each subset is defined based on the body region (e.g., organ) its landmarks belong to and/or the landmarks' physical proximity to the body region. For example, one subset may include landmarks of the hip while another subset may include landmarks of the head. The redundancy model may include one or more predictors that are trained to predict each landmark in the subset using all other landmarks within the subset. All landmarks of the subset are detected, and each detected location is compared to the location for that landmark that would have been predicted by all the other landmarks of the subset. The predictors may be constructed using averaging per subset and/or voting among subsets.

At 208, user interface adapter 118 infers a body section from the detected or predicted landmarks. In some implementations, either the detected or predicted landmarks are used, depending on which landmarks were verified to be valid by the redundancy model. A body section is an anatomical structure (e.g., head, neck, shoulder, trunk, upper limb, lower limb, feet) of an organism (e.g., human) that is defined by one or more landmarks. The detected or predicted landmarks are mapped to a normalized numerical value that represents a body section according to a standardized method. The standardized method may define a "body ruler", wherein each section of the body is represented by a normalized numerical value between two predetermined limits (e.g., from zero to one hundred).

Figure 2B:
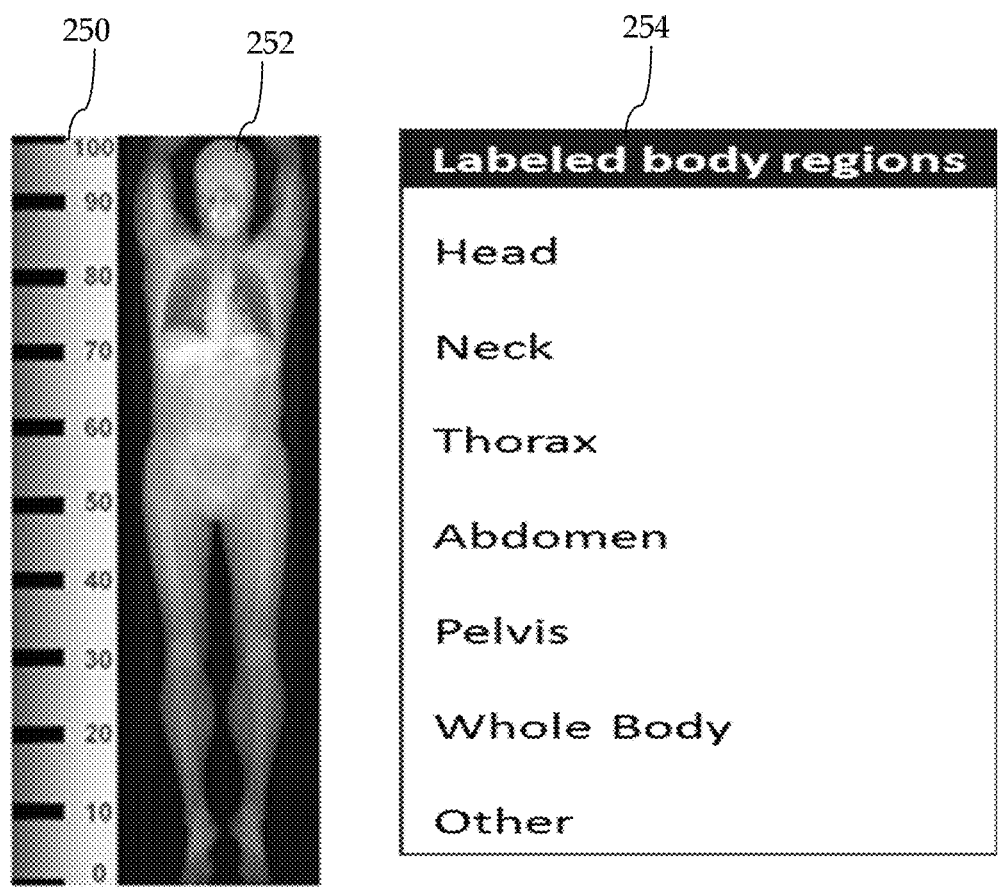
FIG. 2B shows an exemplary body ruler.

FIG. 2B shows an exemplary body ruler 250. The length of the body ruler 250 aligns with the human body 252 positioned in the standing position. The body ruler 250 is divided by equally spaced markings (e.g., 0, 10, 20, . . . , 100) along its length. Each marking corresponds to a normalized numerical value, which may be mapped to a named body section or region. The lower limit (e.g., zero) of the body ruler 250 represents the feet, while the upper limit (e.g., one hundred) of the body ruler the top of the head. Other values may represent other labeled body sections or regions 254 (e.g., head, neck, thorax). For example, the value 90 represents an area of the human head. One or more normalized values may be determined from the body ruler 250 based on the vertical locations of the detected or predicted landmarks on the body 252.

At 210, user interface adapter 118 determines user interface elements based on the inferred body section. The user interface elements may include specific tools and control functions that can be made available to the user via the graphical user interface provided at, for example, workstation 134. A mapping table (or other data structure) may be pre-configured to store predetermined mappings of each body section to one or more specific graphical interface elements.

In some implementations, user interface adapter 118 may look up the mapping table using the normalized values that represent the inferred body section to determine which user interface elements to make available to user. For example, if the inferred body section is the shoulder area (i.e., the shoulder area is present in the current image), the user interface adapter 118 may make available to the user a function to automatically compute images that are sampled along a predetermined axis relevant to the inferred body section, such as the shoulder scapula. Such function may be activated by, for example, a button or menu in the graphical user interface.

At 212, user interface adapter 118 adapts a graphical user interface with the determined user interface elements. The graphical user interface may be displayed at, for example, workstation 134. The graphical user interface may render the one or more current images for display to the user. The graphical user interface may be adapted to make accessible (or display) to the user the determined user interface elements that are relevant to the one or more current images. A list of relevant user interface elements may be displayed in the graphical user interface to enable the user to select the desired user interface element. Irrelevant user interface elements may be disabled, removed or hidden from view to reduce screen clutter and improve efficiency.

Such intelligent anatomy-aware adaptation of the graphical user interface advantageously enables management of the multiplicity of tools available in a radiological image interpretation software. Additionally, a shortlist of relevant tools and/or functions may be presented to the user, making it easier for the user to select the appropriate one and save time, thereby enhancing the efficiency of radiological image interpretation.

Figure 3:
FIG. 3 shows an exemplary screenshot of a graphical user interface adapted by the present framework.

FIG. 3 shows an exemplary screenshot 300 of a graphical user interface adapted by the present framework. After user interface adapter 118 has determined that the heart is present in the current image 302, a function 304 is made available to the user to automatically display a set of suggested views of the heart. The function 304 automatically computes a set of images 306 that are sampled along predetermined axes (e.g., aortic arch, heart long axis and heart short axis) of the heart. The predetermined axes may intersect with an axis 308 defined by the user (or automatically by the framework) on the current image 302. The images 306 may also represent different views (e.g., sagittal, coronal, axial) of each area sampled along each predetermined axis.

Figure 4:
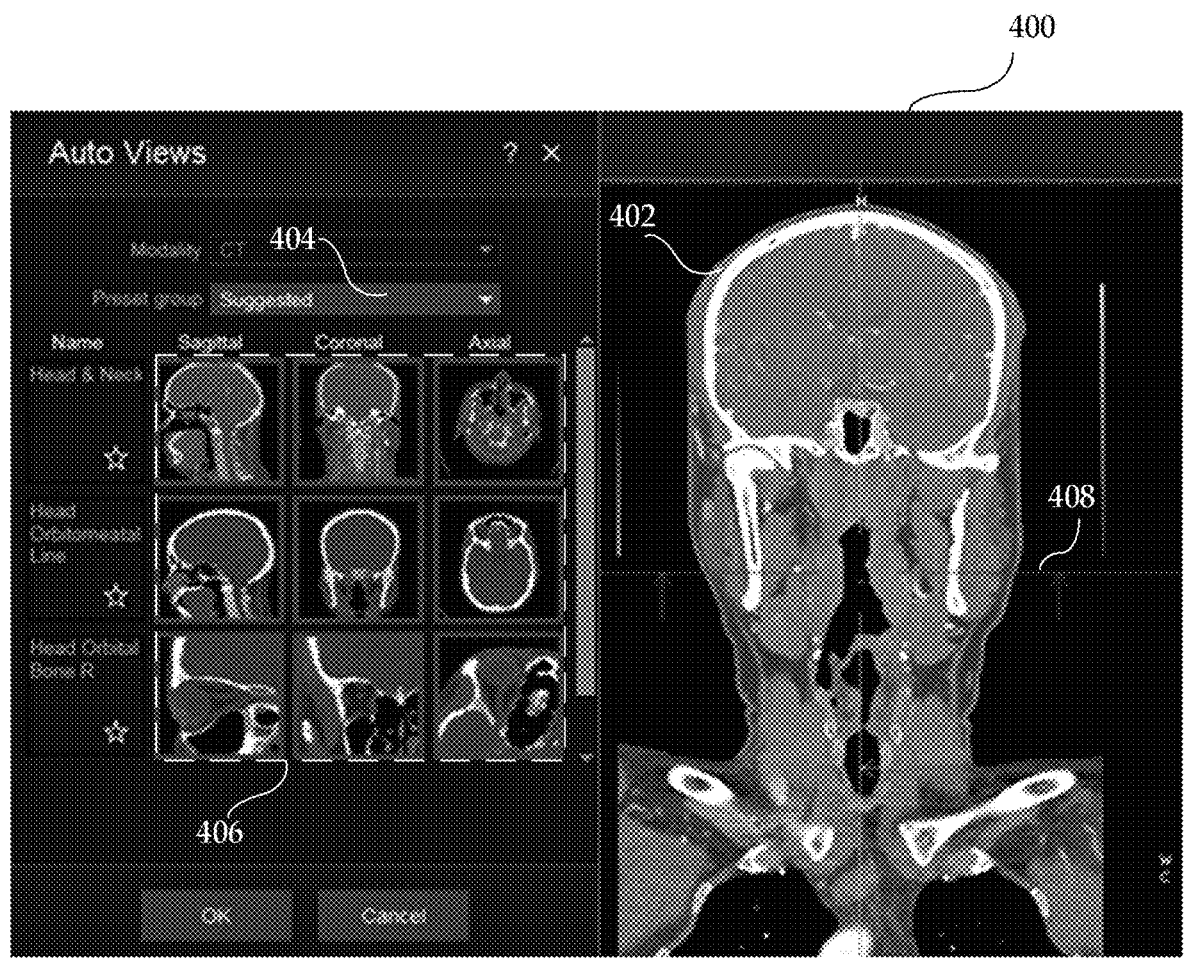
FIG. 4 shows another exemplary screenshot of a graphical user interface adapted by the present framework.

FIG. 4 shows another exemplary screenshot 400 of a graphical user interface adapted by the present framework. After user interface adapter 118 has determined that the head-and-neck region is present in the current image 402, a function 404 is made available to the user to automatically display a set of suggested views of the head and neck. The function 404 automatically computes a set of images (or views) 406 that are sampled along predetermined axes (e.g., head-and-neck, head orbitomeatal line, head orbital bone right) of the head-and-neck region in the current image 402. The predetermined axes may intersect with an axis 408 defined by the user (or automatically by the framework) on the current image 402. The images 406 may represent different views (e.g., sagittal, coronal, axial) of each area sampled along each predetermined axis. The images 406 may be displayed alongside the current image 402 in the graphical user interface.

While the present framework has been described in detail with reference to exemplary embodiments, those skilled in the art will appreciate that various modifications and substitutions can be made thereto without departing from the spirit and scope of the invention as set forth in the appended claims. For example, elements and/or features of different exemplary embodiments may be combined with each other and/or substituted for each other within the scope of this disclosure and appended claims.

What is claimed is:

1. A system for graphical user interface adaptation, comprising:
    a non-transitory memory device for storing computer readable program code; and
    a processor device in communication with the memory device, the processor device being operative with the computer readable program code to perform steps including
        receiving one or more current images,
        detecting landmarks by passing the one or more current images through a trained machine learning model,
        verifying the detected landmarks using a redundancy model to predict landmarks and comparing locations of the predicted landmarks with locations of the detected landmarks to determine reliability of the detected landmarks, wherein the redundancy model comprises one or more predictors trained to predict at least one of the landmarks using other landmarks within a subset,
        inferring a body section based on the detected or predicted landmarks by mapping only vertical locations of the detected or predicted landmarks to a normalized numerical value that represents the body section on a body ruler, wherein a lower limit of the body ruler represents feet and an upper limit of the body ruler represents top of a head,
        determining one or more user interface elements based on the inferred body section, and
        adapting a graphical user interface with the determined one or more user interface elements, including
            displaying a function to automatically compute views sampled along multiple predetermined non-orthogonal axes relevant to the inferred body section, and
            in response to a user selecting the function, computing and displaying the views alongside the one or more current images.

2. The system of claim 1 wherein the one or more current images are acquired by magnetic resonance (MR) imaging, computed tomography (CT), high-resolution computed tomography (HRCT), helical CT, X-ray, angiography, positron emission tomography (PET), fluoroscopy, ultrasound, single photon emission computed tomography (SPECT), or a combination thereof.

3. The system of claim 1 wherein the processor is operative with the computer readable program code to verify the detected landmarks by
in response to determining that a location of at least one of the predicted landmarks does not match a location of at least one of the detected landmarks, determining the detected landmark to be invalid.

4. The system of claim 1 wherein the processor is operative with the computer readable program code to adapt the graphical user interface with the determined one or more user interface elements by removing irrelevant user interface elements from view to reduce screen clutter.

5. The system of claim 1 wherein the processor is operative with the computer readable program code to determine the normalized numerical value from the body ruler by
aligning a length of the body ruler with a body positioned in a standing position, and
determining the normalized numerical value based on locations of the detected or predicted landmarks on the body.

6. A method of graphical user interface adaptation, comprising:
receiving one or more current images;
detecting landmarks by passing the one or more current images through a trained machine learning model;
verifying the detected landmarks using a redundancy model to predict landmarks and comparing locations of the predicted landmarks with locations of the detected landmarks to determine reliability of the detected landmarks, wherein the redundancy model comprises one or more predictors trained to predict at least one of the landmarks using other landmarks within a subset;
inferring a body section based on the detected or predicted landmarks by mapping only vertical locations of the detected or predicted landmarks to a normalized numerical value that represents the body section on a body ruler, wherein a lower limit of the body ruler represents feet and an upper limit of the body ruler represents top of a head;
determining one or more user interface elements based on the inferred body section; and
adapting a graphical user interface with the determined one or more user interface elements, including
displaying a function to automatically compute views sampled along multiple predetermined non-orthogonal axes relevant to the inferred body section, and
in response to a user selecting the function, computing and displaying the views alongside the one or more current images.

7. The method of claim 6 wherein passing the one or more current images through the trained machine learning model comprises passing the one or more current images through a trained convolutional neural network.

8. The method of claim 6 wherein verifying the detected landmarks using the redundancy model to predict the landmarks comprises defining multiple subsets of a whole set of landmarks representing a body.

9. The method of claim 6 wherein adapting the graphical user interface with the determined one or more user interface elements further comprises removing irrelevant user interface elements from view to reduce screen clutter.

10. The method of claim 9 wherein determining the one or more user interface elements based on the inferred body section comprises looking up a mapping table using the normalized numerical value.

11. The method of claim 6 wherein determining the normalized numerical value from the body ruler comprises:
aligning a length of the body ruler with a body positioned in a standing position; and
determining the normalized numerical value based on locations of the detected or predicted landmarks on the body.

12. The method of claim 6 wherein determining the one or more user interface elements based on the inferred body section comprises looking up a mapping table that maps the inferred body section to the one or more user interface elements.

13. The method of claim 6 wherein determining the one or more user interface elements based on the inferred body section comprises determining a function to automatically compute images sampled along at least one predetermined axis that is relevant to the inferred body section.

14. The method of claim 6 wherein adapting the graphical user interface with the determined one or more user interface elements comprises displaying a list of the determined one or more user interface elements and enabling the user to select at least one user interface element from the list.

15. The method of claim 6 wherein the multiple predetermined non-orthogonal axes comprise an aortic arch, a heart long axis and a heart short axis.

16. The method of claim 6 wherein the views comprise sagittal views, coronal views, axial views, or a combination thereof.

17. One or more non-transitory computer-readable media embodying instructions executable by machine to perform operations for graphical user interface adaptation, comprising:
receiving one or more current images;
detecting landmarks by passing the one or more current images through a trained machine learning model;
verifying the detected landmarks using a redundancy model to predict landmarks and comparing locations of the predicted landmarks with locations of the detected landmarks to determine reliability of the detected landmarks, wherein the redundancy model comprises one or more predictors trained to predict at least one of the landmarks using other landmarks within a subset;
inferring a body section based on the detected or predicted landmarks by mapping only vertical locations of the detected or predicted landmarks to a normalized numerical value that represents the body section on a body ruler, wherein a lower limit of the body ruler represents feet and an upper limit of the body ruler represents top of a head;
determining one or more user interface elements based on the inferred body section; and
adapting a graphical user interface with the determined one or more user interface elements, including
displaying a function to automatically compute views sampled along multiple predetermined non-orthogonal axes relevant to the inferred body section, and
in response to a user selecting the function, computing and displaying the views alongside the one or more current images.

18. The one or more non-transitory computer-readable media of claim 17, wherein the trained machine learning model comprises a trained convolutional neural network.

* * * * *